(12) United States Patent
Laufer

(10) Patent No.: US 8,444,569 B2
(45) Date of Patent: May 21, 2013

(54) METHODS AND DEVICES FOR COUNTERACTING HYPOTENSION

(76) Inventor: Michael D. Laufer, Menlo Park, CA (US)

( * ) Notice: Subject to any disclaimer, the term of this patent is extended or adjusted under 35 U.S.C. 154(b) by 1070 days.

(21) Appl. No.: 12/143,435

(22) Filed: Jun. 20, 2008

(65) Prior Publication Data

US 2008/0269787 A1     Oct. 30, 2008

Related U.S. Application Data

(63) Continuation of application No. 10/954,933, filed on Sep. 30, 2004, now Pat. No. 7,410,465.

(51) Int. Cl.
*A61B 5/02* (2006.01)
*A61M 29/00* (2006.01)

(52) U.S. Cl.
USPC ............ 600/499; 600/194; 600/192; 600/191

(58) Field of Classification Search
USPC ................. 600/481, 483, 485, 486, 490–499, 600/300; 606/191, 192, 194, 195, 201, 202
See application file for complete search history.

(56) References Cited

U.S. PATENT DOCUMENTS

| | | | |
|---|---|---|---|
| 4,726,382 A | 2/1988 | Boehmer et al. | |
| 5,275,176 A | 1/1994 | Chandler | |
| 5,509,888 A | 4/1996 | Miller | |
| 6,162,238 A | 12/2000 | Kaplan et al. | |
| 6,299,629 B1 | 10/2001 | Gruenfeld et al. | |
| 6,712,806 B2 | 3/2004 | St. Germain et al. | |
| 6,850,801 B2 * | 2/2005 | Kieval et al. | 607/44 |
| 7,410,465 B2 | 8/2008 | Laufer | |
| 2002/0099409 A1 | 7/2002 | Hui | |
| 2002/0151929 A1 | 10/2002 | Goto et al. | |
| 2003/0060848 A1 | 3/2003 | Kieval et al. | |
| 2003/0199806 A1 | 10/2003 | Kieval | |
| 2004/0106971 A1 | 6/2004 | Schwartz et al. | |
| 2004/0111006 A1 | 6/2004 | Alferness et al. | |
| 2004/0133260 A1 | 7/2004 | Schwartz et al. | |
| 2004/0143319 A1 | 7/2004 | Schwartz et al. | |
| 2004/0204663 A1 | 10/2004 | McLeod | |
| 2004/0230090 A1 | 11/2004 | Hegde et al. | |
| 2006/0084835 A1 | 4/2006 | Laufer | |

FOREIGN PATENT DOCUMENTS

WO     WO 2006/039555     12/2006

OTHER PUBLICATIONS

U.S. Appl. No. 10/954,933, filed Sep. 30, 2004 in the name of Michael D. Laufer, Non-final Office Action mailed Dec. 19, 2006.
U.S. Appl. No. 10/954,933, filed Sep. 30, 2004 in the name of Michael D. Laufer, Non-final Office Action mailed Apr. 27, 2007.
U.S. Appl. No. 10/954,933, filed Sep. 30, 2004 in the name of Michael D. Laufer, Final Office Action mailed Feb. 26, 2008.
U.S. Appl. No. 10/954,933, filed Sep. 30, 2004 in the name of Michael D. Laufer, Notice of Allowance mailed Jun. 9, 2009.
PCT Patent Application No. PCT/US2005/035307 filed Sep. 30, 2005 in the name of Michael D. Laufer, International Search Report and Written Opinion mailed Aug. 28, 2006.

* cited by examiner

*Primary Examiner* — Navin Natnithithadha
(74) *Attorney, Agent, or Firm* — Levine Bagade Han LLP

(57) ABSTRACT

Devices and methods are disclosed to address blood pressure control. More particularly, the present invention relates to correction of transient low blood pressure.

34 Claims, 3 Drawing Sheets

METHODS AND DEVICES FOR COUNTERACTING HYPOTENSION

CROSS-REFERENCE TO RELATED APPLICATIONS

This application is a continuation of U.S. application Ser. No. 10/954,933 filed Sep. 3, 2004 which is incorporated in its entirety herewith.

BACKGROUND OF THE INVENTION

Syncope, commonly known as "passing out," is a common medical condition. While, seizures and strokes can cause actual loss of consciousness a number of less severe conditions or factors may also lead to syncope. However, the potential for serious injury as a result of any temporary loss of consciousness makes syncope a significant medical concern. For example, those individual that are otherwise healthy may face considerable injury as a result of the fall from passing out. Alternatively, a minor fall may have serious consequences if the individual is elderly.

Despite the fact that a number of factors may contribute to syncope, a considerable number of these factors are attributable to the cardiovascular system. For example, a slow heart rate, a long pause between heartbeats, vessel dilation (know also as vasodilatation), dehydration, blood loss, to name a few. These conditions often lead to low blood pressure. Furthermore, many medications cause low blood pressure as a side effect. It is also estimated that as many as 20% of people over the age of 50 have low blood pressure that causes lightheadedness or causes the individual to pass out. Such individuals are at risk especially when they stand up or change position more quickly than their bodies respond to the change in position. This condition is known as orthostatic hypotension. The most common cardiovascular causes for the loss of consciousness are heartbeat related and vessel-related. Pacemakers are commonly used to detect and electrically stimulate the heart in the event of a long pause or low heart rate. However, there remains a need to correct low blood pressure caused by other factors, such as orthostatic hypotension, The invention described herein may alter blood flow as desired and in response to a various number of conditions. For example, and to address the concerns described above, a variations of the present invention addresses low blood pressure caused by orthostatic hypotension. Accordingly, such conditions may include positional changes in the body of the patient, changes in blood flow or pressure within a vessel or vessels, or any other number of conditions.

In both orthostatic hypotension and medication related hypotension there is insufficient blood pressure to adequately supply blood to the brain when the position of the body along with gravity drives blood flow to the lower part of the body. Under normal conditions, to prevent gravity and certain body positions from draining blood to the lower part of the body, blood vessels in the lower part of the body quickly become smaller to redirect flow to the brain. However, the effects of aging or medication impair the body's ability to respond in this manner. Therefore, the effects of these positional body changes become more profoundly noticeable with increasing lightheadedness. Syncope occurs with severely reduced blood flow to the brain. Because the physician is unable to do anything for the patient, these patients are frequently told to stand up or change positions more slowly in order to counteract the effects. Obviously, this is only partially effective. It is estimated that more than half of patients presenting for care in emergency departments with syncope have, as a cause, vasodilatation and orthostatic hypotension. However, these patients often require medical attention for bone fractures, head injuries and other injuries as a result of their syncope.

BRIEF SUMMARY OF THE INVENTION

One variation of the present invention redirects blood flow preventing low blood flow to the brain that results in hypotension, syncope and the related injuries.

A variation of a device in accordance with the invention consists of an implant that alters the flow of blood given a predetermined condition, e.g., given a signal indicating hypotension. As a result, the redirected blood flow supplies the brain with proportionally more of the total flow pumped by the heart. Therefore, the body reacts over time to the positional change lessening the effects of syncope. Eventually, the condition passes, e.g., the body reacts to the change of position, and the device deactivates allowing the body to function normally.

In another variation of a device suited for syncope, the implant presents a variable or fixed flow obstruction downstream from vessels that supply blood to the brain. The obstruction decreases flow in these vessels thereby preferentially directing flow to the brain. The variability of the obstruction to flow can be adjusted as the body reacts to the position change. The implant can be intravascular or extra vascular but shall be enabled to receive signals to determine when to constrict the vessel. It can receive signals from pressure, flow, and/or other detectors that provide for feedback control of the appliance. Alternatively, or in combination, the device may react directly to pressure or flow changes within the body in order to directly vary the flow and/or pressure to the brain based on flow and pressure in the vessel where the appliance was implanted. Naturally, the invention contemplates safety features to make the device acceptable for human use.

It is understood that variations of the details of the design and methods are possible as are adaptations of the invention described herein that would not vary substantially from the invention disclosed herein.

It should also be understood that the device can be used in conjunction with medications that dilate blood vessels to reduce systemic blood pressure so that normal blood flow and pressure can be maintained to the brain while low pressures are provided to the kidneys and other distal organs. In this way, even patients with refractory hypertension can be successfully treated without the most common side effects of orthostatic hypotension and syncope that currently limit the success or acceptance of this therapy.

The present invention modifies the resistance of a vascular system by providing a variable size member, capable of increasing local vascular resistance and redirecting blood flow from the heart. The present invention may redirect flow from within the blood vessel (e.g., a member that increases or decreases the effective vessel lumen diameter), external to the blood vessel (by externally compressing the vessel), in combination with drugs, or via a combination of modes as described herein.

The term variable size is intended to include elastic and inelastic members, distensible members (e.g., members that elastically expand/deform), non-distensible members (e.g., members that do not elastically expand/deform but upon expansion assume a predetermined shape), etc. In one embodiment, the device consists of a variable size member surrounding the aorta or other blood vessel. This device may be implanted percutaneously around a desired vessel location. Alternatively, placement of the device may be performed surgically or minimally invasively. The variable size member is adjusted or self-adjusts when blood pressure reaches a desired level. Additionally, the elasticity of the variable size member may be externally modified to change the vascular resistance. By precisely modifying the properties of the variable size member, blood flow may be redirected as needed.

BRIEF DESCRIPTION THE DRAWINGS

DETAILED DESCRIPTION

Figure 1:
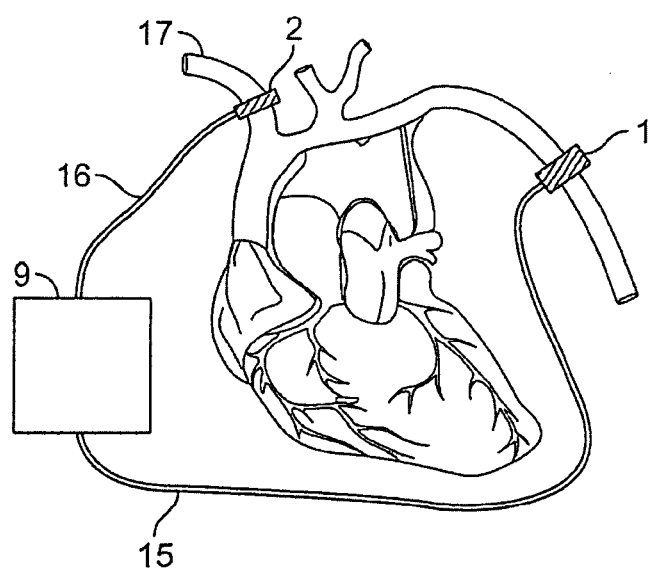
FIG. 1 illustrates a variation of the invention when implanted in the body.

FIG. 1 shows one variation of the invention. A constricting member, e.g., a variable size member (1), suitable for placement around a vessel, for example, around the descending aorta. A sensor (2) monitors the condition of the body to activate the constricting member (e.g., the sensor placement is in or around the carotid (17) or other monitored vessel or the sensor is actually incorporated into the constricting member.) The sensor provides information to the integrating module (9) where it is analyzed and used to constrict the constricting member or relax it. Signals may be sent via wires (15, 16) or through a wireless interface. In this way, blood flow is directed to the vessels proximal to the constricting member. This provides relatively increased blood flow to the vessels supplying the brain, and thereby reduces the sensation of lightheadedness and also reduces syncope with positional change.

Figure 2:
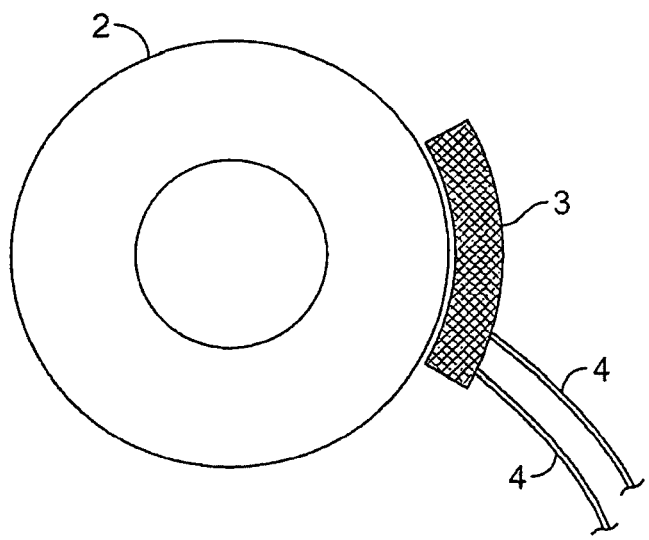
FIG. 2 illustrates an example of a sensor device for use with the inventive device.

FIG. 2 shows one example of a sensor configuration (2). It consists of a strain gauge (3), the output of which is directly proportional to the pressure in the vessel proximate to which it has been placed. This output is sent (e.g., via wires (4)). The sensor can also be constructed to sense flow instead of pressure. Alternatively vessel wall displacement can be measured and used as a surrogate for flow or pressure.

Figure 3:
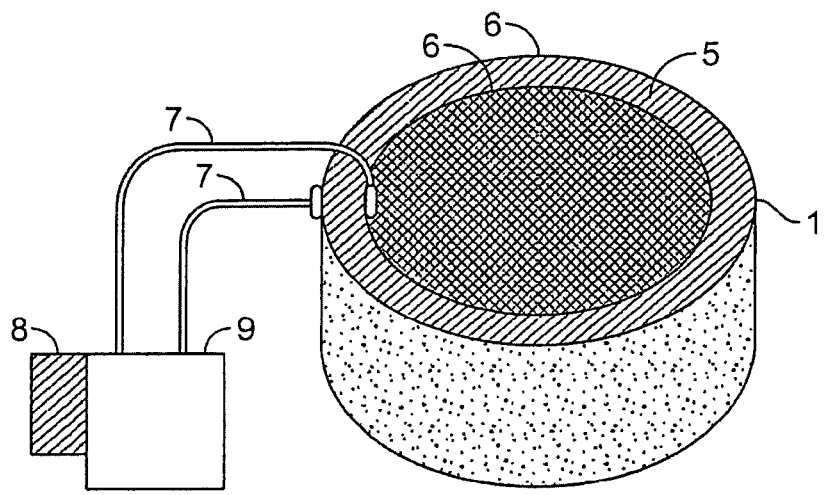
FIG. 3 illustrates a variation of the device for adjusting blood-pressure coupled to an integrating system which may include an electrical source.

FIG. 3 shows an example of a constricting member (1). In this example, the member is constructed with a sandwich (5) of elastomeric, electrically-insulating material such as silicone, rubber, latex, hydrogel, or similar material, with two outer surfaces (6) consisting of electrically conductive material such as graphite, gold, platinum, or the like. Wires (7) are connected between the surfaces (6) and the high-voltage electrical source (8) through the integrating module (9). When a voltage is applied to the surfaces (6), the attractive forces compress the elastomeric material (5) causing it to elongate. Elongation relaxes the constriction.

Figure 4:
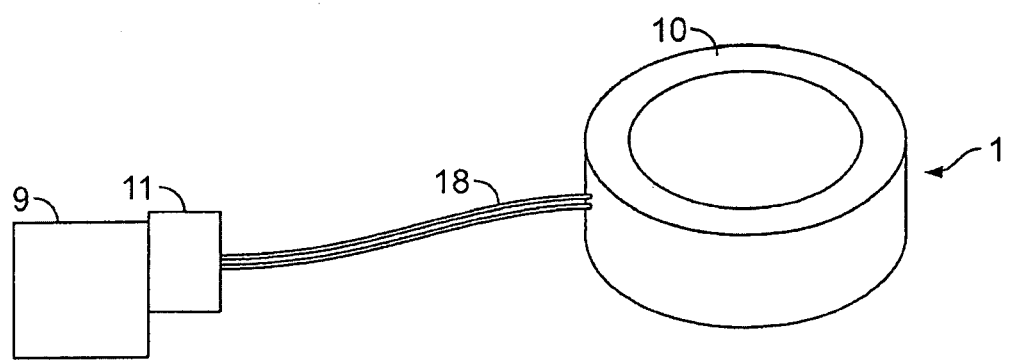
FIG. 4 illustrates an additional variation of the device for adjusting blood-pressure coupled to an integrating system including a pump.

FIG. 4 shows another variation of a constricting member (1). In this embodiment the constricting device consists of an inflatable cuff (10) that is inflated by a pump (11) that is controlled by module (9).

Figure 5:
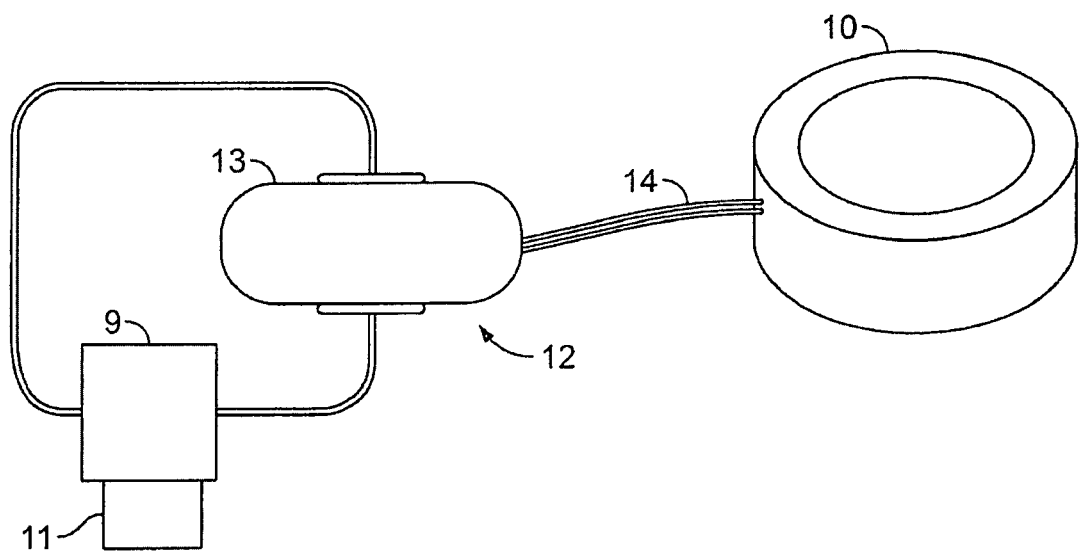
FIG. 5 illustrates the device for adjusting blood-pressure coupled in which a chamber is placed between the pump and constriction device.

FIG. 5 shows a variation where the constricting member (1) is inflated by a pump (12). In this embodiment, the pump consists of a chamber (13) that is filled with gas or fluid. The pump itself may be constructed of an insulating material such as Mylar, with a conductive coating such as a metallic ink or paint. The places where the walls of the chamber (13) meet are insulated so as to keep each surface electrically distinct and insulated from one another. The pump is activated by sending a voltage from the high-voltage source (8) as in FIG. 3 to the surfaces of the chamber (13). The charges on the surfaces attract one another and move the fluid within chamber (13) to the constricting cuff (10) through connecting member (14). The cuff may be deflated by pressure within the aorta when the electrical charge is turned off, or actively by charging both surfaces of the pump equally, causing the surfaces to repel, and causing the chamber (13) to increase in size, drawing the fluid or gas back into the chamber (13). The cuff can be variably inflated by modulating the voltage across the diaphragm. Therefore, the constriction can be varied and the pressure modulated by changing the voltage across the chamber (13).

Figure 6:
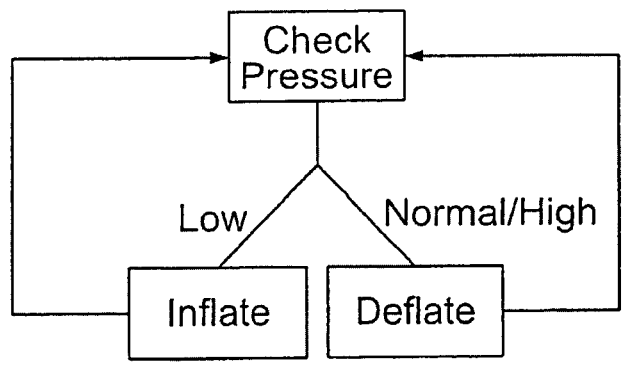
FIG. 6 illustrates a flow-chart schematic of an example of the feedback used in the control module to control blood pressure and flow control with the device described herein.

FIG. 6 shows a flow-chart schematic of the feedback used in the control module (9) to accomplish blood pressure and flow control with the pump and constricting device as shown in FIGS. 4 and 5 or with an integrated constriction device as shown in FIG. 3.

In addition to the above discussion, the invention includes, but is not limited to the following: A method of reducing blood flow in a first portion of the body to increase blood flow in a second portion of the body in response to a condition as described herein. The method may comprise contracting a diameter of a vessel in response to a condition of or within the body.

In the above method the event may comprise generating a signal in response to a change to a condition of or within the body. For example, the reduction of blood flow in the first part of the body may comprise reducing flow within a portion of the aorta that is downstream of blood vessels whose purpose is to provide blood for the brain. The signal may comprise a decrease in blood flow to the brain, positional changes in the body of the patient, changes in blood flow or pressure within a vessel or vessels, or any other number of conditions.

The devices described herein generally redirect blood-flow as a result a change to a condition within or of the body. In one example, the device comprises a variable size member having a passage therethrough, the variable size member configured for placement within the body; the variable size member is adapted to reduce a diameter of the passage in response to the change to the condition within or of the body.

In these devices and methods, the conditions may be those as described above, or other conditions as required by the specific treatment sought.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

The above illustrations are examples of the invention described herein. Because of the scope of the invention, it is specifically contemplated that combinations of aspects of specific embodiments or combinations of the specific embodiments themselves are within the scope of this disclosure.

What is claimed is:

1. A device for adjusting flood-pressure in a patient comprising:
a variable size member having, a body capable of placement around a first body vessel portion where the variable size member includes an electrically conductive material located on a surface of an elastic material, where the electrically conductive material is configured to compress an elastic material to expand and contract the variable size member and where the electrically conductive material is located on two separate surfaces of the variable size member;
the variable size member configured to expand and contract in response to changes in intra-luminal vessel pressure of at least a second body vessel portion.

2. The device according to claim 1, further comprising a chamber adapted to adjust an elastic, compliance of the variable size member by filling with a medium.

3. The device according to claim 2, further comprising a reservoir in fluid communication with the chamber, the reservoir comprising the medium.

4. The device according to claim 2 wherein the medium is selected from a group comprising, a gas and liquid.

5. The device according to claim 1 wherein the body comprises an elastic, biocompatible material.

6. The device according to claim 5 wherein the body comprises a material selected from a group comprising silicone and urethane.

7. The device according to claim 2 wherein the body comprises a resilient material.

8. The device according to claim 1 wherein the body comprises an inelastic material.

9. The device according to claim wherein the body comprises Mylar and is filled with a second elastic material or gas.

10. The device according to claim 1 wherein pressure of the chamber is between 50 and 100 mmHg when filled at least partially.

11. The device according to claim 1 wherein the device is sized and shaped so as to allow 5 to 100 ml of medium to fill the chamber.

12. The device according to claim 1 further, comprising a media port disposed on the body for adding and removing, a medium, 13. The device according to claim I further, comprising, an adjustment member to variably secure the variable size member about the vessel.

14. The device according to claim 1, further comprising a sensor in electrical communication with the variable size member.

15. The device according to claim 14, where the sensor is configured to detect changes in pressure.

16. The device according to claim 14, where the sensor is selected from a group consisting of a strain gauge, a flow sensor, and a displacement sensor.

17. The device according to claim 1, further comprising a pump in fluid communication with the variable size member, where the pump is configured to expand and contract the variable size member.

18. The device according to claim 17, where the pump drives a gas or liquid into the variable size member.

19. The device according to claim 17, where the pump comprises an electrically conductive material, where the conductive material compresses upon application of a current.

20. The device according to claim 19, where the electrically conductive material comprises Mylar.

21. The device according to claim 20, where the electrically conductive material comprises a form of a Mylar sac.

22. The device according to claim 1, where the variable size member comprise an distensible member.

23. The device according to claim 1, where the variable size member comprise a non-distensible member.

24. A method for redirecting, blood flow in a first portion of a body lumen to alter blood pressure in a second portion of a body lumen comprising:
connecting a variable size member to the first body lumen;
the variable size member having an internal chamber containing a media and altering blood flow in the first body lumen using the variable size member where the variable size member includes an electrically conductive material located on a surface of an elastic material, where the electrically conductive material is configured to compress an elastic material to expand and contract the variable size member and where the electrically conductive material is located on two separate surfaces of the variable size member.

25. The method according to claim 24 wherein connecting the variable size member comprises connecting the variable size member externally to the first body lumen.

26. The method according to claim 24 wherein connecting the variable size member comprises connecting the variable size member within the first body lumen.

27. The method according to claim 24 wherein the variable size member is connected with or without the ability to adjust the variable size member.

28. The method according to claim 24 wherein the media is selected from a group comprising a gas and liquid.

29. The method according to claim 24, where the variable size member comprises a resilient material.

30. The method according to claim 24, wherein the variable size member is composed of an elastic, biocompatible material.

31. The method according to claim 24, wherein the internal chamber has a pressure of between 50 and 100 mmHg when at least partially filled.

32. The method according to claim 24, wherein the variable size member chamber contains 5 to 100 ml of media.

33. The method according to claim 24, wherein a pressure within the body lumen is adjusted by the adjustment member.

34. The method according to claim 24, where the variable size member is placed within the first body lumen.

* * * * *

UNITED STATES PATENT AND TRADEMARK OFFICE
CERTIFICATE OF CORRECTION

PATENT NO. : 8,444,569 B2  
APPLICATION NO. : 12/143435  
DATED : May 21, 2013  
INVENTOR(S) : Laufer Page 1 of 1

It is certified that error appears in the above-identified patent and that said Letters Patent is hereby corrected as shown below:

In the Claims:

In claim 1, Col. 5, line 2, please replace "flood-pressure" with -- blood-pressure --.

Signed and Sealed this
Seventeenth Day of September, 2013

Teresa Stanek Rea
*Deputy Director of the United States Patent and Trademark Office*